(12) United States Patent
Kopetzki et al.

(10) Patent No.: US 6,284,484 B1
(45) Date of Patent: Sep. 4, 2001

(54) PROCESS FOR THE PRODUCTION OF PROTEINS IN SOLUBLE FORM BY MODULATION OF AN INDUCIBLE PROMOTER

(75) Inventors: Erhard Kopetzki, Penzberg; Günther Schumacher, Bernried, both of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 07/725,943

(22) Filed: Jun. 27, 1991

Related U.S. Application Data

(63) Continuation of application No. 07/215,724, filed on Jul. 6, 1988, now abandoned.

(30) Foreign Application Priority Data

Jul. 20, 1987 (DE) ................................................. 37 23 992

(51) Int. Cl.[7] .................................................. C12P 21/02
(52) U.S. Cl. .................................................. 435/69.1
(58) Field of Search .................................. 435/69.1, 244, 435/252.33, 14, 29

(56) References Cited

FOREIGN PATENT DOCUMENTS 159123  10/1985  (EP) .
192988   9/1986  (EP) .

OTHER PUBLICATIONS

Winnacker, E.L., From Genes to Clones: Introduction to Gene Technology, VCH, Germany, 1987. pp 239–317.*
Maston, F., "The Purification of Eucaryctic Polypeptides Synthesized in Escherichia coli", Biochem. J. 240,pp 1–12 1986.*
Luck, D. N. et al., "Synthesis of Borine Prolactin in Escherichia coli", DNA, vol. 5, No. 1, pp 21–28, 1986.*
Bagdasrian, M.M., "Activity of the Hybrid brp–lac (tac) promoter of Escherichia coli in Pseudomonas putida. Conteuction of broad–hostrange, controlled expression vectors", Gene 26 pp 273–282 1983.*
Kopetzki et al., Mol Gen. Genet., 216 149–155 (1989).
Schein et al., Biotechnology, 6, 291–294 (1988).
Mizukami et al., Biotechnology Letters, 8:9, 605–610 (1986).

* cited by examiner

Primary Examiner—Terry McKelvey
Assistant Examiner—Gerald G. Leffers, Jr.
(74) Attorney, Agent, or Firm—Fulbright & Jaworski, LLP

(57) ABSTRACT

The present invention provides a process for the expression in appropriate host cells of recombinant DNA which is under the control of an inducible promotor. In order to obtain the soluble form of recombinant protein, which would usually be obtained in insoluble form, the induction of the promotor is limited to less than 10% of the maximum induction in comparison with a standard system and the transcription rate of the DNA coding for the protein is correspondingly limited.

30 Claims, 2 Drawing Sheets

FIG. 1

```
                                                                          60
ATG ACT ATT TCT GAT CAT CCA GAA ACA GAA CCA AAG TGG TGG AAA GAG GCC ACA ATC TAT
Met Thr Ile Ser Asp His Pro Glu Thr Glu Pro Lys Trp Trp Lys Glu Ala Thr Ile Tyr
                                                                         120
CAA ATT TAC CCA GCA AGT TTT AAA GAC TCC AAT AAC GAT GGC TGG GGT GAT TTA AAA GGT
Gln Ile Tyr Pro Ala Ser Phe Lys Asp Ser Asn Asn Asp Gly Trp Gly Asp Leu Lys Gly
                                                                         180
ATC ACT TCC AAG TTG CAG TAT ATT AAA GAT CTT GGC GTT GAT GCT ATT TGG GTT TGT CCG
Ile Thr Ser Lys Leu Gln Tyr Ile Lys Asp Leu Gly Val Asp Ala Ile Trp Val Cys Pro
                                                                         240
TTT TAT GAC TCT CCT CAA CAA GAT ATG GGG TAT GAT ATA TCT AAC TAC GAA AAG GTC TGG
Phe Tyr Asp Ser Pro Gln Gln Asp Met Gly Tyr Asp Ile Ser Asn Tyr Glu Lys Val Trp
                                                                         300
CCC ACA TAC GGT ACC AAC GAG GAC TGT TTT GAG CTA ATT GAC AAG ACT CAT AAG CTG GGT
Pro Thr Tyr Gly Thr Asn Glu Asp Cys Phe Glu Leu Ile Asp Lys Thr His Lys Leu Gly
                                                                         360
ATG AAA TTC ATC ACC GAT TTG GTT ATC AAC CAC TGT TCT ACA GAA CAC GAA TGG TTC AAA
Met Lys Phe Ile Thr Asp Leu Val Ile Asn His Cys Ser Thr Glu His Glu Trp Phe Lys
                                                                         420
GAG AGC AGA TCC TCG AAG ACC AAT CCG AAG CGT GAC TGG TTC TTC TGG AGA CCT CCT AAG
Glu Ser Arg Ser Ser Lys Thr Asn Pro Lys Arg Asp Trp Phe Phe Trp Arg Pro Pro Lys
                                                                         480
GGT TAT GAC GCC GAA GGC AAG CCA ATT CCT CCA AAC AAT TGG AAA TCT TTC TTT GGT GGT
Gly Tyr Asp Ala Glu Gly Lys Pro Ile Pro Pro Asn Asn Trp Lys Ser Phe Phe Gly Gly
                                                                         540
TCA GCT TGG ACT TTT GAT GAA ACT ACA AAT GAA TTT TAC CTC CGT TTG TTT GCG AGT CGT
Ser Ala Trp Thr Phe Asp Glu Thr Thr Asn Glu Phe Tyr Leu Arg Leu Phe Ala Ser Arg
                                                                         600
CAA GTT GAC TTG AAT TGG GAG AAT GAA GAC TGC AGA AGG GCA ATC TTT GAA ACT CCT GTT
Gln Val Asp Leu Asn Trp Glu Asn Glu Asp Cys Arg Arg Ala Ile Phe Glu Ser Pro Val
                                                                         660
GGA TTT TGG CTG GAC CAT GGT GTA GAT GGT TTT AGA ATC GAT ACC GCT GGT TTG TAT TCG
Gly Phe Trp Leu Asp His Gly Val Asp Gly Phe Arg Ile Asp Thr Ala Gly Leu Tyr Ser
                                                                         720
AAA CGT CCT GGT TTA CCA GAT TCC CCA ATT TTT GAC AAA ACC TCG AAA TTA CAA CAT CCA
Lys Arg Pro Gly Leu Pro Asp Ser Pro Ile Phe Asp Lys Thr Ser Lys Leu Gln His Pro
                                                                         780
AAT TGG GGG TCT CAC AAT GGT CCT AGG ATT CAT GAA TAT CAT CAA GAA CTA CAC AGA TTT
Asn Trp Gly Ser His Asn Gly Pro Arg Ile His Glu Tyr His Gln Glu Leu His Arg Phe
                                                                         840
ATG AAA AAC AGG GTG AAA GAT GGT AGA GAA ATA ATG ACA GTC GGT GAA GTT GCC CAT GGA
Met Lys Asn Arg Val Lys Asp Gly Arg Glu Ile Met Thr Val Gly Glu Val Ala His Gly
                                                                         900
AGT GAT AAT GCT TTA TAC ACC AGT GCA GCT AGA TAC GAA GTC AGC GAA GTT TTC TCC TTC
Ser Asp Asn Ala Leu Tyr Thr Ser Ala Ala Arg Tyr Glu Val Ser Glu Val Phe Ser Phe
                                                                         960
ACG CAC GTT GAA GTT GGT ACC TCG CCA TTT TTC CGT TAT AAC ATA GTG CCC TTC ACC TTG
Thr His Val Glu Val Gly Thr Ser Pro Phe Phe Arg Tyr Asn Ile Val Pro Phe Thr Leu
                                                                        1020
AAA CAA TGG AAA GAA GCC ATT GCA TCC AAC TTT TTG TTC ATT AAC GGT ACT GAT AGT TGG
Lys Gln Trp Lys Glu Ala Ile Ala Ser Asn Phe Leu Phe Ile Asn Gly Thr Asp Ser Trp
                                                                        1080
GCT ACC ACC TAC ATC GAG AAT CAC GAT CAA GCC CGG TCA ATT ACG AGA TTT GCT GAC GAT
Ala Thr Thr Tyr Ile Glu Asn His Asp Gln Ala Arg Ser Ile Thr Arg Phe Ala Asp Asp
                                                                        1140
TCG CCA AAG TAC CGT AAA ATA TCT GGT AAG CTG TTA ACA TTG CTA GAA TGT TCA TTG ACA
Ser Pro Lys Tyr Arg Lys Ile Ser Gly Lys Leu Leu Thr Leu Leu Glu Cys Ser Leu Thr
                                                                        1200
GGT ACG TTG TAT GTC TAT CAA GGT CAG GAG ATA GGC CAG ATC AAT TTC AAG GAA TGG CCT
Gly Thr Leu Tyr Val Tyr Gln Gly Gln Glu Ile Gly Gln Ile Asn Phe Lys Glu Trp Pro
                                                                        1260
ATT GAA AAG TAT GAG GAC GTT GAT GTG AAA AAC AAC TAC GAG ATT ATC AAA AAG AGT TTT
Ile Glu Lys Tyr Glu Asp Val Asp Val Lys Asn Asn Tyr Glu Ile Ile Lys Lys Ser Phe
                                                                        1320
GGT AAA AAC TCG AAG GAA ATG AAG GAT TTT TTT AAA GGA ATC GCC CTA CTT TCT AGA GAT
Gly Lys Asn Ser Lys Glu Met Lys Asp Phe Phe Lys Gly Ile Ala Leu Leu Ser Arg Asp
                                                                        1380
CAT TCG AGA ACT CCC ATG CCA TGG ACC AAA GAT AAG CCC AAT GCT GGA TTT ACT GGC CCA
His Ser Arg Thr Pro Met Pro Trp Thr Lys Asp Lys Pro Asn Ala Gly Phe Thr Gly Pro
                                                                        1440
GAT GTT AAA CCT TGG TTT TTC TTG AAT GAA TCT TTT GAG CAA GGA ATC AAT GTT GAG CAG
Asp Val Lys Pro Trp Phe Phe Leu Asn Glu Ser Phe Glu Gln Gly Ile Asn Val Glu Gln
                                                                        1400
GAA TCC AGA GAT GAT GAC TCA GTT CTC AAT TTT TGG AAA AGG GCC TTG CAA GCC AGA AAG
Glu Ser Arg Asp Asp Asp Ser Val Leu Asn Phe Trp Lys Arg Ala Leu Gln Ala Arg Lys
                                                                        1560
AAA TAT AAG GAA CTT ATG ATT TAT GGT TAC GAT TTC CAA TTC ATT GAT TTA GAC AGT GAC
Lys Tyr Lys Glu Leu Met Ile Tyr Gly Tyr Asp Phe Gln Phe Ile Asp Leu Asp Ser Asp
                                                                        1620
CAG ATC TTT AGC TTC ACT AAA GAG TAC GGA GAC AAG ACG CTG TTT GCT GCT TTG AAT TTC
Gln Ile Phe Ser Phe Thr Lys Glu Tyr Gly Asp Lys Thr Leu Phe Ala Ala Leu Asn Phe
                                                                        1680
AGT GGC GAA GAA ATT GAA TTC AGC CTC CCA AGA GAA GGT GCT TCT TTA TCT TTT ATT CTT
Ser Gly Glu Glu Ile Glu Phe Ser Leu Pro Arg Glu Gly Ala Ser Leu Ser Phe Ile Leu
                                                                        1740
GGA AAT TAT GAT GAT ACT GAC GTT TCC TCC AGA GTT TTG AAA CCA TGG GAA GGT AGA ATC
Gly Asn Tyr Asp Asp Thr Asp Val Ser Ser Arg Val Leu Lys Pro Trp Glu Gly Arg Ile

TAC CTC GTC AAA TAA
Tyr Leu Val Lys End
```

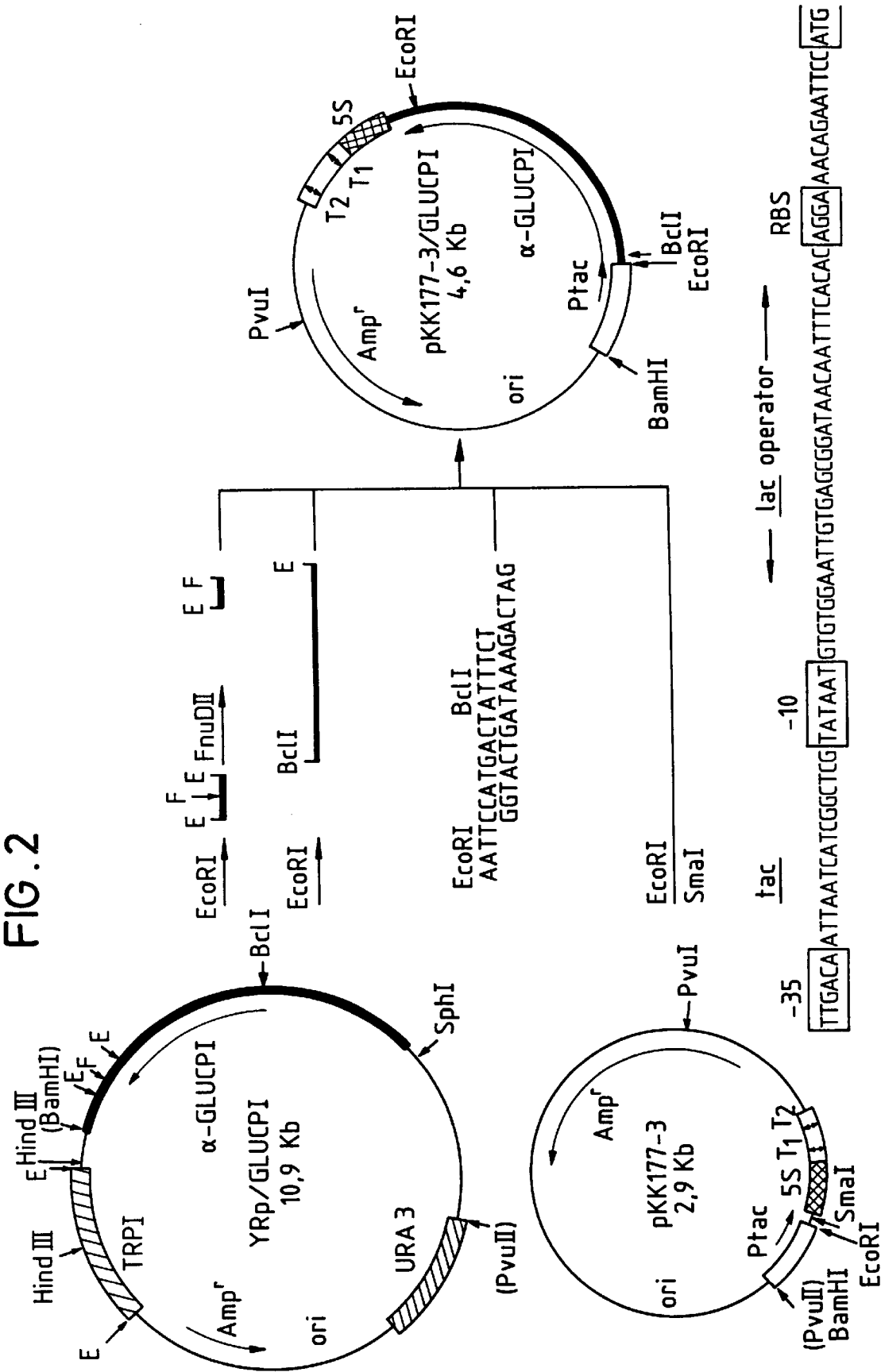

PROCESS FOR THE PRODUCTION OF PROTEINS IN SOLUBLE FORM BY MODULATION OF AN INDUCIBLE PROMOTER

This application is a continuation of application Ser. No. 07/215,724, filed Jul. 6, 1988, now abandoned.

The present invention is concerned with a process for the expression of recombinant DNA which is under the control of an inducible promoter in a host cell.

By means of recombinant DNA technology, many problems in the production of proteins can be solved or considerably simplified. Briefly, the DNA sequence (gene) coding for the desired protein is integrated into an expression vector and expression of the protein is controlled via regulatory sequences, especially via promoters.

Especially preferred promotors, with which high yields of homologous and heterologous proteins can be obtained, are those which, as a rule, show both high and controllable activity. Such promotors include natural, hybrid and bacteriophage promotors, for example the lac, lacuv5, trp, tac, trc, rac, phoA, mgl, $\lambda$-$P_L$, $\lambda$-$P_R$, $T_5$, $T_7$ and SP6 promoters, when the host cell is Escherichia coli.

The activity of these promotors can be controlled, for example, by inducers (substrates, substrate analogues), by the temperature, or by the amount of available bacteriophage RNA polymerase. Using these, one can ensure, e.g., that heterologous protein is expressed only during particular periods of cultivation. For example, one can control expression so that it does not take place at the beginning of cultivation of the micro-organism used as host. Such control is especially advantageous when the heterologous protein is toxic for the host cell. When the expression of toxic heterologous proteins in hosts, such as Escherichia coli, is desired, it is usual to proceed in such a manner that, after a culturing phase in which the promotor is present in a repressed state, an appropriate inducer is added for the complete activation of the promotor. The promotor and thus the expression of the foreign protein is often induced in the late logarithmic to early stationary growth phase of the host cell after the achievement of an appropriate high cell density (biomass) (Mitzukamie et al., Biotech. Lett., 8, 611–614/1986). In the case of the use of the lac, lacuv5, tac, trc and rac promotor, as inducer there is added, for example, isopropyl-$\beta$-D-thiogalactopyranoside (IPTG) in a concentration of about 1 mM (Miller, Experiments in Molecular Genetics, Cold Spring Harbor Laboratory, Cold Spring Harbor, N.Y., 1972). The expression of protein which is under lac repressor synthesis (lacI$^q$) increases with increasing inducer concentration (IPTG: 0, 2 and 20 mM) (Luck et al., DNA, 5, 21–28/1986). The repression of the trp promotor by tryptophan is removed by removal of the co-repressor tryptophan (tryptophan-free medium) and/or by induction with 3,$\beta$-indolylacrylic acid (IAA) in a concentration of 20 to 50 mg/l. (Smith et al., Gene, 32, 321–327/1984; Mosteller et al., Symp. Quant. Biol., 35, 461–466/1970).

However, it has been shown that this process does not: lead for all homologous and heterologous proteins to satisfactory yields of proteins of the desired properties,, such as solubility, natural conformation and possibly biological activity. Whereas for some enzymatically-active proteins, for example $\beta$-galactosidase, $\beta$-lactamase, chloramphenicol acetyltransferase (CAT), creatinase and penicillin acylase, solubility and high enzyme activity are achieved after expression in Escherichia coli, with the use of the same conditions and of the same promotors, in the case of other proteins only small amounts of soluble proteins or no soluble protein at all or even biologically inactive product are obtained. Such effects are observed, for example, in the case of $\alpha$-glucosidase, prochymosin, the heavy and light chains of antibodies, immunoglobulins, urokinase, tPA, interferon, growth hormone, fusion proteins from $\beta$-galactosidase and HIV antigens and human insulin polypeptides (Marston, Biochem. J., 240, 1–12/1986).

However, it has been shown that these proteins are certainly present in large amounts in the appropriate cell extracts but are insoluble and/or display no biological activity.

As the cause for the low expression of soluble and especially of active protein in Escherichia coli, there has been discussed, for example, the denaturing of the foreign protein to give refractile bodies (inclusion bodies), i.e. to give insoluble protein aggregates, as well as proteolysis of the foreign gene product by the cell's own proteases (Carriers et al., Trends in Biotechnology, 1, 109–113/1983). In order here to provide some help, it has been proposed by Mitzukamie et al. (Biotech. Lett., 8, 605–610/1986), that for the expression of beta interferon (IFN-$\beta$) in Escherichia coli under the control of the trp promotor, to carry out the fermentation at 20° C. At this temperature, the yield of active IFN-$\beta$ increases. However, it is a disadvantage of this process that fermentation times of at least 4 days are needed in order to obtain activities for which the working up is worthwhile.

Furthermore, it has been suggested to use host cells from which the proteolytic system responsible for the cleavage of the gene product is absent. Thus, for example, a lon mutant of Escherichia coli can be used as host cell. Such mutants are deficient with regard to a protease occurring in the wild type. Since, however, at least 7 further proteases are present in Escherichia coli (Swamy et al., J. Bacteriol., 149, 1027–1033/1982), the process is then only appropriate when the protein to be expressed is not cleaved by these other proteases. Furthermore, the choice of appropriate host cells is very limited.

Furthermore, it has been suggested to increase the expression by increasing the copy number of the expression vector to such an extent that the proteases are inundated by large amounts of protein formed and, consequently, only inactivate a comparatively small percentage of the protein. However, a disadvantage of this method is that the expression must be increased immensely within only 1 or 2 generations and cannot be carried out for a comparatively long period of time (Trends in Biotechnology, 1, 109–113/1983).

Therefore, it is an object of the present invention to avoid the above-described disadvantages of the prior art and to make possible the production of soluble and biologically-active proteins.

Thus, according to the present invention, there is provided a process for the expression in appropriate host cells of recombinant DNA which is under the control of an inducible promotor, wherein, for the production in soluble form of proteins which, under usual gene-technological production conditions, are obtained in insoluble form, the induction of the promotor is limited to less than 10% of the maximum induction in comparison with a standard system, which results a limited transcription rate of the DNA coding for the protein and a reduced rate of the synthesis of said protein.

By the limitation of the induction of the promotor, it is possible to limit the formation of refractile bodies and, instead, to produce soluble and active protein in large amounts. Without such a limitation of the speed of expression, complete induction admittedly leads to very rapid formation of protein. These proteins, however are present in the form of refractile bodies or as inactive proteins or protein fragments.

In the case of the process according to the present invention, the induction of the promotor is preferably limited to less than 5% and an especially preferred embodiment limits it to less than 1% of the maximum induction in comparison with a standard system.

As standard system, one may use a vector in which the foreign gene to be expressed has been replaced by another heterologous or homologous gene which, in this system (equal to the host cell), expresses soluble, active protein, in which case this "standard gene" must then, of course, be under the control of the same promotor as the foreign gene. Examples of standard gene includes β-lactamase, CAT and creatinase. As another standard system, the host cell itself (without vector) could also be used when it already contains, chromosomally integrated, a standard gene under comparable control of the promotor intended for use (see the following Example 2, the β-galactosidase gene of *Escherichia coli* encoded by the natural lac-operon.

All host cells in which the expression of a recombinant DNA under the control of an inducible promotor is possible can be used for the expression of the recombinant DNA. The expression is preferably carried out in *Escherichia coli* and especially preferably in *Escherichia coli* strains which carry a lac-$I^q$ gene. An example is *Escherichia coli*, DSM 2102, which is transformed with plasmid pePA 119 (DMS 3691P). In the following description, this strain is referred to as ED82-$I^q$. The induction thereby takes place most favorably in the logarithmic growth phase. As promoters for the process according to the present invention, in *Escherichia coli* there can be used natural, hybrid and bacteriophage promotors. Preferably, there are used the lac, lacuv5, trp, tac, trc, rac, phoA, mgl, $\lambda$-$P_L$, $\lambda$-$P_R$, $T_5$, $T_7$ and SP6 promotors.

A maximum induction of β-galactosidase in *Escherichia coli* wild type cells ($lacI^+Z^+Y^+$) is achieved with an inducer concentration of 0.1 to 1 mM IPTG (R. Knippers, Molekulare Genetik, pub. Georg Thieme Verlag, Stuttgart, New York, 1985). In the presence of an intact lactose permease ($lacY^+$), IPTG is actively transported into the cell at a concentration more than 50 fold of the extracellular concentration so that, intracellularly there exists an inducer concentration of more than 5 mM (Miller, Experiments in Molecular Genetics, Cold Spring Harbor Laboratory, Cold Spring Harbor, N.Y., 1972).

According to a preferred embodiment of the present invention, limited induction is brought about by lowering the effective intracellular inducer concentration less than 10%, preferably to less than 5% and especially to less than 1% in comparison with a standard system as defined above. Maximum induction is then achieved when, after doubling of the inducer concentration, the specific enzyme activity of the standard increases less than 15%.

The limitation of the induction can be brought about, for example, by limited addition of inducer. In the case of the use of the lac promotor or of a promotor derived therefrom, as inducer there is added IPTG, preferably in a concentration of less than 0.01 mM.

According to a further preferred embodiment, the limitation of the induction takes place by limitation of the active transport of the inducer through the cell membrane. A defective transport system can, for example, be obtained by making a mutation in the lactose permease gene (lacY) of *Escherichia coli*. In this case, as inducer there can be used, for example, IPTG or lactose. In the case of a defective transport system, the intracellular IPTG concentration then corresponds to the extracellular concentration (Miller, Experiments in Molecular Genetics, Cold Spring Harbor Laboratory, Cold Spring Harbor, N.Y., 1972). In spite of defective lactose permease, lactose can be taken up to a small extent via the thiomethylgalactosidase I and arabinose permeation system (Rotman et al., J. Mol. Biol. 36, 247–260/1968, Messer, J. Bacteriol. 120, 266–272/1974).

There is preferably used the lac promotor or a promotor derived therefrom in a host cell which carries a mutation in this lactose permease gene (lacy).

As host cells, there are especially preferably used cell of *Escherichia coli*, which contain a defective lactose permease gene and, in addition, the lac-$I^q$ gene, for example, *Escherichia coli* strain ED82-$I^q$, DSM 2102, transformed with plasmid DSM 3691P, which encodes for the lac-$I^q$ gene. For induction lactose is added to the culture medium in a concentration of less than 1%. The lactose present in the medium is scarcely metabolized but it suffices for the induction of the promotor.

The limitation of the induction can also be achieved by the addition of inducers, which are metabolized by the cells and thus lose their inducing action.

A further embodiment of the limitation of the induction in the process according to the present invention involves controlling the activity of promoters by influencing the effector-promotor exchange action. The intracellular concentration of the inducer is thereby not decisive but its affinity for the repressor or vice versa controls. Lowering of the inducer-repressor exchange action can, for example, be achieved by the use of a micro-organism which carries a repressor mutant gene, which encodes for a repressor-protein with a changed repressor-inducer binding constant. In such a process, the lac promotor is preferred, as well as a micro-organism which carries a lac-repressor mutant gene ($lacI^s$).

A further embodiment uses promoters which possess a catabolite-activator protein (CAP) site, the affinity of the catabolite activator protein to the promotor thereby being reduced.

The effect according to the present invention can be increased by additional measures which affect the growth of the cells in the case of the fermentation and by the point of time at which the inducer is added. Thus, the expression of soluble, active α-glucosidase takes place by very slow induction of the tac promotor and additional increasing measures which influence the growth.

The speed of growth of cells can be influenced, for example, by the nature of the medium (complete or minimal media, for example DYT, LB, M9CAA and M9), the carbon source (for example sugar, glycerol and peptone), the nitrogen source (for example ammonium sulphate, amino acids and peptone), the pH value of the medium, the temperature, the amount of available oxygen, as well as the origin of the strain (mutations). Changed growth rates can also be broughtabout by overlapping effects. Thus, for example, by decomposition of carbon sources, the medium becomes strongly acidic (pH 4.8) resulting in slowed growth rates.

BRIEF DESCRIPTION OF THE FIGURES

FIG. 1 is the nucleotide sequence and amino acid sequence derived therefrom of α-glucosidase pI; and FIG. 2 is the construction of the α-glucosidase pI plasmid pKK177-3 /GLUCPI for expression in *Escherichia coli*.

DETAILED DESCRIPTION OF PREFERRED EMBODIMENTS

Expression of α-glucosidase in *Escherichia coli*

For the manipulation of DNA, standard methods are used such as are described by Maniatis et al.(1982) in Molecular Cloning, (Cold Spring Harbor Laboratory, Cold Spring Harbor, N.Y. 11724). The molecular biological reagents used are employed according to the instructions of the manufacturer.

EXAMPLE 1

Construction of the α-glucosidase pI expression vector pKK177 3/GLUCPI

The structural gene of α-glucosidase pI (FIG. 1) from Bakers' yeast is constructed via an adaptor (correct binding between promotor and N-terminus) and two α-glucosidase-coding DNA fragments of the plasmid YRp/GLUCPI, DSM 4173P (FIG. 2). The 3'-untranslated region of the α-glucosidase from yeast is removed up to 25 bp.

For this purpose, the plasmid YRp/GLUCPI is digested with EcoRI and BclI and the BclI/EcoRI fragment (1.7 kb), as well as the EcoRI fragment (about 0.3 kb), isolated. The EcoRI fragment is post-cleaved with FnuDII and the EcoRI/FnuDII fragment (0.13 kb) isolated.

The vector pKK177-3 DSM 3062, is cleaved with EcoRI and SmaI. Into the resulting vector fragment (2.85 kb) the BclI/EcoRI fragment the EcoRI/FnuDII fragment, as well as the synthetic DNA fragment

5'-AATTCCATGACTATTTCT -3'

3'-GGTACTGATAAAGACTAG -5' are ligated.

The desired construction was identified and isolated on 5-bromo-4-chloroindolyl-α-D-glucopyranoside indicator plates α-XGl, 40 mg/liter) and 1 mM IPTG on the basis of low α-glucosidase activity in ED82-$I^q$.

The correct construction of the α- GLUCPI gene is confirmed by restriction analysis. The plasmid has the designation pKK177-3/GLUCPI. The host strain ED82-$I^q$ has no α-glucosidase activity under the test conditions.

EXAMPLE 2

Expression of yeast α-glucosidase PI in *Escherichia coli* under standard conditions For the heterologous expression of α-glucosidase pI from yeast, there was used the *Escherichia coli* K-12 strain ED82-$I^q$ which contains the vector pKK177-3/GLUCPI. The experiments were carried out in roller cultures (20 ml reagent glass with 5 ml of medium) in LB medium (Maniatis et al., Molecular Cloning, Cold Spring Harbor Laboratory, 1982) with 40mg/liter of ampicillin at 37° C. The cultures were inoculated with 50 μl of overnight culture and, upon achieving a cell density of $OD^{550}$ of from 0.5 to 0.6, were induced with 5 mM IPTG (end-concentration). After 2 to 3 hours 0,5 ml culture samples were harvested, the cell pellets washed with 10 mM phosphate buffer pH 6.8 and immediately frozen.

α-glucosidase and β-galactosidase assay

Frozen all pellets were resuspended in 0.25 ml 10 mM phosphate buffer pH 6.8 with 1 mM EDTA and disrupted by sonification. After centrifugation soluble active α-glucosidase was assayed in the supernatant in 0.1 M phosphate buffer pH 6.8 at 25° C. with 2mM p-nitrophenyl-α-D-glucopyranoside (PNPG) as substrat. For the calculation of spezific activities the protein was estimated according to the micro-biuret method (Zamenhof, Methods Enzymol. 696–704/1957) with bovine serum albumin as a standard. Specific activities are expressed as nanomoles of substrate hydrolyzed per minute per milligram of protein. The β-galactosidase was determined analogously using 2-nitrophenyl-β-D-galactopyranoside as substrate instead of PNPG. The chromosomally coded β-galactosidase in ED82-$I^q$ served for the control of the course of induction of the lac operon.

EXAMPLE 3 a) Dependency of the yield of active protein (α-glucosidase pI and β-galactosidase) depending upon the period of induction and upon the IPTG inducer concentration.

Working was carried out as described in Example 2, the inducer concentration (IPTG) and the period of culturing thereby being varied. The results obtained are shown in the following Table I.

TABLE 1

| inducer | Yield of active protein (mU/mg protein) Fermentation period (min) | | | | | | 450 | |
|---|---|---|---|---|---|---|---|---|
| IPTG | 40 | | 85 | | 145 | | α- | |
| (mM) | α-Gluc | β-Gal | α-Gluc | β-Gal | α-Gluc | β-Gal | Gluc | β-Gal |
| 0 | 175 | 1 | 132 | 2 | 140 | 12 | 11 | 17 |
| 0.01 | 193 | 2 | 194 | 6 | 156 | 15 | 8 | 46 |
| 0.033 | 120 | 6 | 152 | 16 | 123 | 27 | 7 | 57 |
| 0.066 | 83 | 12 | 113 | 27 | 102 | 33 | 7 | 85 |
| 0.1 | 82 | 24 | 102 | 36 | 106 | 47 | 6 | 140 |
| 0.33 | 60 | 48 | 86 | 67 | 102 | 100 | 12 | 281 |
| 0.66 | 48 | 50 | 77 | 83 | 100 | 116 | 10 | 334 |
| 1 | 58 | 66 | 80 | 96 | 88 | 117 | 9 | 384 |
| 3 | 62 | 76 | 78 | 95 | 90 | 116 | 9 | 405 |
| 6 | 68 | 74 | 84 | 114 | 97 | 135 | 6 | 436 |

The results show that the specific activity of the β-galactosidase (internal control) continuously increases with increasing inducer concentration and increasing period of induction. In contradistinction to β-galactosidase, the specific activity of the β-glucosidase achieves a maximum at a concentration of 0.01 mM of IPTG.

b) Dependency of the yield of active protein (α-glucosidase and β-galactosidase) upon the lactose inducer concentration Working was carried out as described in Example 2, the inducer concentration (lactose) thereby being varied. The results obtained are shown in the following Table II.

TABLE II

| inducer | yield of active protein (mU/mg protein) | |
|---|---|---|
| lactose (%) | α-Gluc | β-Gal |
| 0 | 54 | 1 |
| 0.05 | 110 | 5 |
| 0.1 | 134 | 9 |
| 0.5 | 199 | 36 |
| 1 | 223 | 38 |
| 2 | 13 | 1080 |

The results show that the β-galactosidase is fully induced (internal control) by a lactose concentration of 2%. In contradistinction thereto, in the case of the same inducer concentration, the α-glucosidase only achieves a specific activity of 5% of the maximum achievable specific enzyme activity.

EXAMPLE 4

Dependency of the yield of active protein (α-glucosidase and β-galactosidase) on the pH value and upon the concentration of inducer IPTG Working was carried out as described in Example 2, the pH value at the time of induction being adjusted by the addition of Tris-HCl or phosphate buffer (end concentration 0.1 M) and an inducer concentration of 0.01 mM IPTG (Table IIIa) and 0.5% lactose (Table IIIb) being used. The results obtained are given in the following Tables IIIa and IIIb.

TABLE III

| | yield of active protein (mU/mg protein) | |
|---|---|---|
| | α-Gluc | β-Gal |
| a) pH value inducer IPTG 0.01 (mM) | | |
| 8.7 | 3 | — |
| 8.0 | 168 | 1 |
| 7.0 | 53 | 1 |
| 6.3 | 79 | 1 |
| 6.0 | 264 | 1 |
| 5.6 | 384 | 1 |
| b) inducer lactose (0.5%) | | |
| 8.0 | 179 | 14 |
| 7.0 | 346 | 17 |
| 6.0 | 867 | 17 |
| 5.5 | 969 | 19 |
| 5.0 | 1629 | 5 |

It can be seen that at the pH range optimal for culturing *Escherichia coli* (7.0 to 7.5), there is surprisingly obtained the lowest yield of active protein. The optimum ranges are from 4.8 to 5.6, as well as from 7.5 to 8.5. Furthermore, the enzyme activity is increased by a factor of 8 in comparison with the sole induction with lactose (0.5%). (Table II, line 4, compared with Table IIIb), line 5).

EXAMPLE 5

Dependency of the yield of active protein (α-glucosidase and β-galactosidase) upon the culturing temperature Working was carried out as described in Example 2, the temperature and the inducer IPTG (0.01 mM) and lactose (0.5%) being varied. The results are given in the following Table IV.

TABLE IV

| | yield of active protein (mU/mg protein) temperature (° C.) | | | | | | | |
|---|---|---|---|---|---|---|---|---|
| | 22 | | 27 | | 32 | | 37 | |
| inducer | α-Gluc | β-Gal | α-Gluc | β-Gal | α-Gluc | β-Gal | α-Gluc | β-Gal |
| IPTG (mM) 0.06 | n.d. | n.d. | 1500 | 16 | 935 | 24 | 125 | 75 |
| lactose (%) 0.5 | 2200 | 6 | 1560 | 5 | 1050 | 9 | 460 | 22 | n.d. = not determined

The results show that the specific activity of the β-galactosidase (internal control) is not influenced by the culturing temperature. Surprisingly, however, the specific activity of the α-glucosidase increases in the case of lower culturing temperatures.

EXAMPLE 6

Dependency of the yield of active protein (α-glucosidase and β-galactosidase) upon the medium and period of culturing Working was carried out as described in Example 2, the medium being varied and 0.5% lactose being used as inducer. The results obtained are shown in the following Table V.

TABLE V

| | yield of active protein (mU/mg protein) culture period (h) | | | | | |
|---|---|---|---|---|---|---|
| | 3 | | 6 | | 20 | |
| Medium | α-Gluc | β-Gal | α-Gluc | β-Gal | α-Gluc | β-Gal |
| LB | 600 | 4 | 1500 | 13 | 4 | 124 |
| M9CAA** | 30 | — | 110 | 4 | 2000 | 113 |
| M9* | 10 | — | 20 | — | 3000 | 83 |

*M9 minimal medium per-liter:
$Na_2HPO_4$ 6 g.
$KH_2PO_4$ 3 g.
NaCl 0.5 g.
$NH_4Cl$ 1 g.
$MgSo_4 \cdot 7H_2O$ 1 mM
thiamine 1 mg/l.
glucose 0.2%
**M9CAA M9CAA minimal medium M9 with 0.5% casamino acids

EXAMPLE 7

Dependency of the yield of active protein (α-glucosidase and β-galactosidase) upon the carbon source

TABLE VI

| | yield of active protein (mU/mg protein) culture period (h) | | | |
|---|---|---|---|---|
| carbon | 2.5 | | 6 | |
| source | α-Gluc | β-Gal | α-Gluc | β-Gal |
| glucose | 414 | — | 649 | 3 |
| maltose | 1535 | 7 | 1982 | 7 |
| glycerol | 833 | 12 | 2838 | 14 |
| maltose/glycerol | 1312 | 12 | 1744 | 9 |

EXAMPLE 8

Preferred culturing conditions for active α-glucosidase

For the synthesis of active α-glucosidase, $ED_{82}$-$I^q$ with plasmid-coded α-glucosidase was cultured in LB medium or in minimal medium at 37° C. up to an $OD^{550}$ of 0.4 to 0.6. Thereafter, the culture was cooled (20 to 30° C.), induced with lactose (end concentration 0.5%) and either a carbon source (end concentration 1 to 2%; preferably glycerol and/or maltose) added thereto or the pH value lowered with phosphate buffer (0.1 M) to pH 4.8 to 5.5 and the cells cultured at 20 to 30° C. up to a cell density of $OD^{550}$ of 3 to 5. The results obtained are given in the following Table VII.

TABLE VII

| medium | carbon source (%) | culture time (h) | temperature (° C.) | inducer lactose (%) | yield of active protein (mU/mg protein) α-Gluc | β-Gal |
|---|---|---|---|---|---|---|
| LB | glycerol | 20 | 27 | 0.5 | 5500 | — |
| LB | glycerol | 20 | 37 | 0.5 | 5000 | — |
| LB | — | 6 | 27 | 0.5 | 4000 | 110 |
| M9 | — | 20 | 37 | 0.5 | 3500 | 110 |
| M9 | glycerol | 20 | 37 | 0.5 | 4000 | n.d. |
| M9 | gly/mal | 20 | 37 | 0.5 | 3900 | n.d. | n.d. = not determined

It will be understood that the specification and examples are illustrative but not limitative of the present invention and that other embodiments within the spirit and scope of the invention will suggest themselves to those skilled in the art.

A deposit was made under the terms of the Budapest Treaty of the following materials with the Deutsche Sammlung von Mikroorganismen, Mascheroder Weg 1B, 3300 Braunschweig, Germany. The deposited materials are listed with their accession numbers and submission:

Escherichia coli I$^q$ (DSM 2102) (May 27, 1981)
vector pKK 177/3 (DSM 3062) (Sep. 26, 1984)
plasmid pePA119 (DSM 3691) (Apr. 9, 1986)
plasmid Yrp-Gluc.pI (DSM 4173P) (Jun. 29, 1987)

We claim:

1. A process for the expression of a protein in a transformed Escherichia coli host cell containing a DNA sequence encoding said protein and controlled by an inducible promoter, said process comprising limiting induction of said promoter to less than 10% of the maximum induction of said promoter thereby producing a greater amount of soluble and active forms of said protein than in the absence of the limited induction of said promoter.

2. The process of claim 1, comprising limiting induction of said promoter to less than 5% of the maximum induction.

3. The process of claim 1, comprising limiting induction of said promoter to less than 1% of the maximum induction.

4. The process of claim 1, wherein said host cell is an Escherichia coli cell containing a lac-I$^q$ gene.

5. The process of claim 1, wherein said host cell is an Escherichia coli DSM 2102 cell.

6. The process of claim 1, comprising limiting induction during the logarithmic growth phase of said host cell.

7. The process of claim 4, wherein said promoter is a naturally occurring promoter.

8. The process of claim 7, wherein said promoter is a lac, lacuv 5, trp, tac, trc, rac, phoA, mgl, λ-P$_1$, λ-P$_r$, T5, T7, or SP6 promoter.

9. The process of claim 1, comprising limiting induction by restricting addition of inducer.

10. The process of claim 8, wherein said promoter is a lac promoter or a derivative of a lac promoter.

11. The process of claim 1, wherein said promoter is a lac promoter or a derivative of a lac promoter and said limiting induction comprises adding isopropyl-β-D-thiogalactopyranoside in a concentration less than 0.01 mM.

12. The process of claim 1, wherein said promoter is a lac promoter and said limiting induction comprises adding lactose at a concentration of less than 1%.

13. The process of claim 1, wherein said host cell is an Escherichia coli ED82-I$^q$ cell.

14. The process of claim 1, wherein said host cell is a microorganism containing a lac promoter and a lac repressor mutant gene lacI$^S$.

15. The process of claim 1, wherein said promoter has a catabolite activator protein site and said promoter has reduced affinity for the catabolite activator protein.

16. The process according to claim 1, wherein the maximum induction of said promoter is determined by comparison with a standard system of said transformed Escherichia coli host cell, wherein said standard system consists of the expression of beta-galactosidase in said host cell under the control of the same inducible promoter using an inducer concentration of 0.1 to 1 mmol/l IPTG.

17. The process of claim 16, comprising limiting induction of said promoter to less than 5% of the maximum induction.

18. The process of claim 16, comprising limiting induction of said promoter to less than 1% of the maximum induction.

19. The process of claim 16, wherein said host cell is an Escherichia coli cell containing a lac-I$^q$ gene.

20. The process of claim 16, wherein said host cell is an Escherichia coli DSM 2102 cell.

21. The process of claim 16, comprising limiting induction during the logarithmic growth phase of said host cell.

22. The process of claim 19, wherein said promoter is a naturally occurring promoter.

23. The process of claim 22, wherein said promoter is a lac, lacuv 5, trp, tac, trc, rac, phoA, mgl, λ-P$_1$, λ-P$_r$, T5, T7, or SP6 promoter.

24. The process of claim 16, comprising limiting induction by restricting addition of inducer.

25. The process of claim 23, wherein said promoter is a lac promoter or a derivative of a lac promoter.

26. The process of claim 16, wherein said promoter is a lac promoter or a derivative of a lac promoter and said limiting induction comprises adding isopropyl-B-D-thiogalactopyranoside in a concentration less than 0.01 mM.

27. The process of claim 16, wherein said promoter is a la promoter and said limiting induction comprises adding lactose at a concentration of less than 1%.

28. The process of claim 16, wherein said host cell is an Escherichia coli ED82-I$^q$ cell.

29. The process of claim 16, wherein said host cell is a microorganism containing a lac promoter and a lac repressor mutant gene lacI$^S$.

30. The process of claim 16, wherein said promoter has a catabolite activator protein site and said promoter has reduced affinity for the catabolite activator protein.

* * * * *